United States Patent [19]

Gallagher, deceased

[11] Patent Number: 4,960,497
[45] Date of Patent: Oct. 2, 1990

[54] APPARATUS AND METHOD FOR MINIMIZING THE EFFECT OF AN ELECTROLYTE'S DISSOLVED OXYGEN CONTENT IN LOW RANGE OXYGEN ANALYZERS

[75] Inventor: John P. Gallagher, deceased, late of Palm Beach, Fla., Janice M. Gallagher, legal representative

[73] Assignee: Delta F Corporation, Woburn, Mass.

[21] Appl. No.: 410,111

[22] Filed: Sep. 20, 1989

[51] Int. Cl.⁵ ............................................. G01N 27/42
[52] U.S. Cl. ................................ 204/153.16; 204/412
[58] Field of Search ........................ 204/412, 432, 1 T

[56] References Cited

U.S. PATENT DOCUMENTS 3,929,587 12/1975 Gallagher ........................ 204/432 X

*Primary Examiner*—G. L. Kaplan
*Attorney, Agent, or Firm*—Samuels, Gauthier & Stevens

[57] ABSTRACT

A reservoir of electrolyte is placed in communication with the electrolyte of an electrochemical or electrolytic cell which is adapted for oxygen analysis. A cathode is placed in the electrochemical cell and an anode is placed in the reservoir, with a potential of 1.5 VDC applied between them. At the cathode a mild electrolysis of water occurs and a film of highly reactive hydrogen is generated. Similarly, oxygen is generated at the anode. The equilibrium partial pressure of the dissolved oxygen in the electrolyte of the electrochemical or electrolytic cell is reduced via its consumption in the reaction with the hydrogen to form water. Oxygen generated in the reservoir is allowed to effervesce. Thus, an electrolyte devoid of dissolved oxygen can be maintained which allows an accurate analysis of the gaseous sample stream.

20 Claims, 1 Drawing Sheet

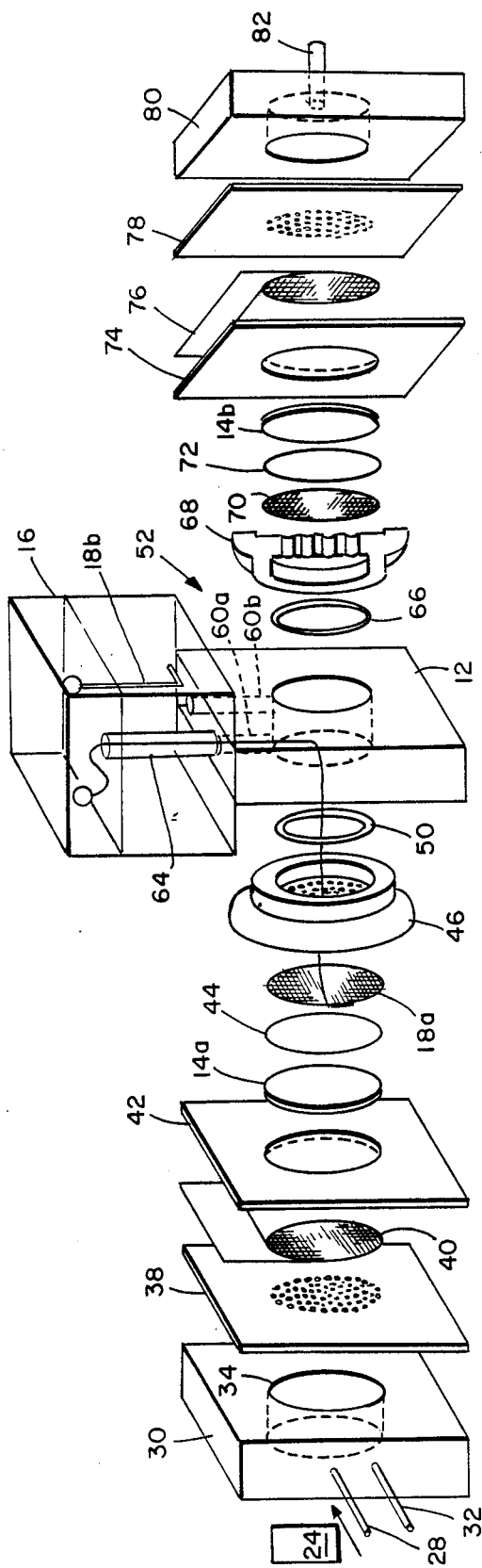
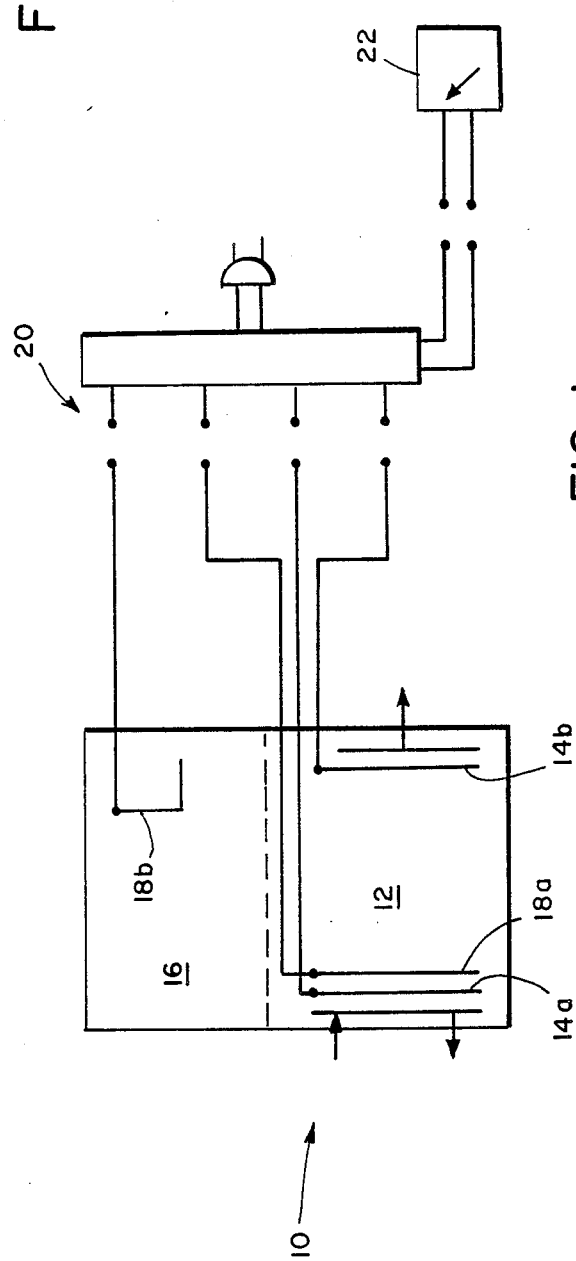
FIG. 2
FIG. 1

APPARATUS AND METHOD FOR MINIMIZING THE EFFECT OF AN ELECTROLYTE'S DISSOLVED OXYGEN CONTENT IN LOW RANGE OXYGEN ANALYZERS

BACKGROUND OF THE INVENTION

An electrochemical cell, in its simplest terms, consists of an anode (the oxidizing electrode), a cathode (the reducing electrode) and an electrolyte. In order for the electrochemical or electrolytic cell to function, the electrolyte must be compatible with the mechanisms of oxidation and reduction at the electrodes. As well, it must provide a conductive path for the transport of ionic species between the electrodes.

The electrochemical cell concept is broadly applied in industrial and scientific operations. Electrolytic cells are used in electroplating, water purification, and the production of high purity gases and metals while galvanic cells (batteries and fuel cells) provide a convenient means of energy storage and generation.

Also, due to their very high level of sensitivity, electrochemical cells are used for measurement in a variety of analytical procedures and many laboratory and process control instruments depend on the electrochemical cell as the sensing element for their function.

In the design of any electrochemical cell the choice of electrolyte is of importance. Considerable study has been given to identify the compositions and concentrations of electrolytes which will produce the best results in a wide variety of cell systems and applications.

In the utilization of electrochemical cells as sensing elements in analytical instruments, the requirement to maintain a consistent electrolyte composition is commonly required in order to ensure the accuracy of measurement. For example, in the determination of oxygen in fluids by electrochemical methods, this has been found to be the case. Further, in low temperature caustic electrolyte systems, the sample stream introduced into the electrolytic cell commonly contains components other than the one to be analyzed. These other components, for example, carbon dioxide, contained as a component in a stream for oxygen analysis result in a neutralization reaction forming neutralization products. This reduces the transfer of ions through the electrolyte causing drift of measurement in analysis. The problems of the neutralization products being formed in the electrolyte were overcome by the invention disclosed in U.S. Pat. No. 3,929,587. That invention allowed for oxygen level determinations in the presence of acid gases.

For some applications, it is desirable to be able to measure accurately and over long periods of time, levels of oxygen in the ppb range. Electrolytes inherently contain dissolved oxygen. This is not a problem when measuring in the ppm range. However, when measuring in the low ppb range, say between 1–10 ppb, the dissolved oxygen in the electrolyte contributes significantly to the measurement of oxygen from the gas sample.

SUMMARY OF THE INVENTION

The present invention relates to a method and apparatus for the removal of dissolved oxygen from an electrolyte. This dissolved oxygen when removed allows for an accurate reading of oxygen concentration in the gas sample.

The cell includes sensing electrodes for the component in the fluid stream to be analyzed. The sensing electrode (which functions as a cathode) is generally any semi-permeable electrode catalytically specific to oxygen. A non-specific cathode may be used as long as the reduction of oxygen at the cathode is proportional to the oxygen entering the electrolytic cell.

A barrier cathode, such as a platinum wire mesh, is interposed between the sensing cathode and the electrolyte in the cell cavity. An electrode, an anode, such as a suspended platinum rod, is located in the electrolyte reservoir. An electrolytic path is established between the first and second electrodes through the common electrolyte. The cathode and anode are connected to a power source. A potential of less than 1.7 VDC (for 1M KOH), preferably 1.5 VDC, is applied between them. The voltage applied is slightly less than the voltage required to fully electrolyze water into the products of gaseous diatomic hydrogen and oxygen. At 1.5 VDC, hydrogen and oxygen are not produced in their fully gaseous states, but are generated in a highly reactive and unstable "nascent" state. The "nascent" hydrogen which is produced at the cathode residing in the electrochemical cell reacts with the dissolved oxygen in the electrolyte to form water. The oxygen formed at the anode effervesces from the reservoir. The oxygen in the stream to be measured is placed in contact with the sensor on the side opposite that which the cathode creating the hydrogen is placed. Thus, fluid flow communication is still provided between the stream carrying the oxygen to be measured and the electrolyte, but the interposition of the cathode with its coating of active hydrogen eliminates any dissolved oxygen in the electrolyte from contacting the sensing electrode whereby it could interfere with the sensing mechanism.

BRIEF DESCRIPTION OF THE DRAWINGS

FIG. 1 is a functional block diagram of an embodiment of the invention; and

FIG. 2 is an exploded perspective view of an embodiment of the invention.

DESCRIPTION OF THE PREFERRED EMBODIMENT(S)

Referring to FIG. 1, a block functional diagram of the electrolytic system 10, of the preferred embodiment of the invention is shown and includes an electrolytic cell 12 having sensing electrodes 14a and 14b disposed therein. A reservoir 16 is in fluid flow communication with the cell 12 and includes an electrode 18b. An electrode 18a is disposed in cell 12. The load for the electrodes 14a and 14b is provided by a DC circuit and power conditioner 20. The electrolyte and the cell 12 with the electrodes 14a and 14b completes the electrolytic circuit. The power conditioner 20 also provides the potential for electrodes 18a and 18b and the electrolyte common to the cell 12 and reservoir 16 by a separate DC circuit. Although not shown, the power conditioner will include the appropriate resistors, amplifiers, etc. in order to control specifically the potential applied to each set of electrodes. A meter 22 communicates with electrodes 14a and 14b via the power conditioner 20 to provide a direct reading corresponding to the electrolytic oxidation and reduction of the component to be analyzed.

Referring to FIG. 2, the cell 12 and reservoir 16 are shown in greater detail. The gaseous stream containing the component to be analyzed flows from a source 24 through an inlet 28 and into an inlet plate 30. The inlet plate 30 also includes outlet 32. The inlet plate 30 includes a cavity-like recess 34 through which the gaseous stream flows. An apertured diffusion plate 38 meters the diffusion of the separator gas in the sample stream flowing through the inlet plate 30. A current collector 40 is sandwiched between the diffusion plate 38 and an electrode retainer plate 42 having an aperture therein. The electrode 14a is received in the aperture. A permeable separator 44 is interposed between the electrode 14a and the platinum screen electrode 18a. An electrolyte plate 46 having flow passages therein abuts the electrode 18a on one side and on the other side receives an O ring 50. A housing 52 generally comprises the lower electrolytic cell 12 and the upper reservoir 16. Conduits 60a and 60b are formed in the cell 12 and are received in the bottom of the reservoir 16. A sleeve 64 in the reservoir is placed over the conduit 60a to isolate electrode 18a from 18b, and through which the wire for the electrode 18a passes. The electrode 18b is also secured in any suitable manner within the reservoir 16. The electrolyte in the cell 12 and the reservoir 16 are in fluid flow communication with one another only via the conduit 60b.

On the other side of the housing 12 are an O-ring 66, an electrolyte plate 68, having flow passages therein, a stainless steel screen 70, a permeable separator 72, such as an asbestos separator, the electrode 14b, an electrode retainer plate 74, a current collector 76, a gas diffuser plate 78 and a downstream gas cavity end plate 80 including a gas vent 82.

The end plate 82 does not communicate with a source of supply gas or the like but rather it simply includes the gas vent 82. The electrode 14b may be of a different structure and composition than the electrode 14a. The diffusion plate 78 may have apertures therein configured differently from that of 38 in that the diffusion rate of the gas through this diffusion plate is not as critical as the diffusion rate through the upstream diffuser plate.

In the operation of the invention, an electrolyte such as a solution of one molar potassium hydroxide-one molar potassium carbonate is introduced into the reservoir and electrolytic cavity. The conduit 60b provides fluid flow communication therebetween. The current collectors 40 and 76, specifically, the extending tabs on the current collectors, are connected to the power conditioner 20 through appropriate connectors (not shown). The polarities are as indicated in the drawings. This establishes a first electrolytic path between the sensing electrodes 14a and 14b.

The electrodes 18a and 18b are connected to the power conditioner 20 through appropriate connectors (not shown). Again, the polarities are as indicated in the drawings. This establishes a second electrolytic path between the electrodes 18a and 18b and through the common electrolyte.

Referring to the second electrolytic path, resistance to current flow that results in this particular cell configuration is equivalent to approximately 10 ohms. A potential of approximately 1.5 volts is applied across the electrodes 18a, which is a platinum screen that functions as a cathode (negative terminal) and the electrode 18b which is a platinum wire that functions as an anode (positive terminal). The potential at the electrodes is controlled by the power conditioner. The current produced by this electrolytic circuit is equivalent to the equilibrium rate of $O_2$ availability at the cathode.

A gaseous stream flows from the source 24 into the inlet 28 at a rate of about 2 scfh. A flow rate of between 1.0 to 3.0 scfh is preferred. The gas may be at a temperature of between 0° to 150° F. and a pressure of less than 15.7 psia. For illustrative purposes, the invention will be described in reference to a gaseous composition of three ppb oxygen, the remainder nitrogen. The sensor 14a, which functions as a cathode, may be any semi-permeable electrode catalytically specific to oxygen. A non-specific cathode may be used as long as the reduction of oxygen at the cathode is proportional to the oxygen entering the electrolytic cell. With three ppb oxygen partial pressure across the diffusion barrier 38, $1 \times 10^{-6}$ cc per hour of oxygen flows to the cathode sensor 14a. The rate of oxygen exposed to the sensor 14a will result in a current flow of approximately 5 nano-amps in the cell. The power conditioner 20 communicating with the collecting screens 40 and 76 has an applied potential of 1.3 VDC. The sensor electrode 14b, which functions as an anode, is illustrated as the same type of semi-permeable electrode catalytically specific to oxygen, such as a carbon-Teflon electrode. However, a solid metal electrode, such as platinum, gold, etc., may be used. In this embodiment, the oxygen is reduced at the electrode 14a. The applied potential provides the driving force for the transport of the anions or hydroxyl ions. The hydroxyl ions complete the first electrolytic path between the sensors 14a and 14b.

Inherent in the electrolyte is dissolved oxygen. Measuring oxygen in the ppb range, the dissolved oxygen can contribute significantly and provide a reading error. That is, unless the dissolved oxygen contribution is eliminated, the dissolved oxygen in the electrolyte will also be reduced at the electrode 14a thereby providing an erroneous reading.

The electrode 18a, the barrier electrode, is interposed between the electrolyte and one side of the sensing electrode 14a. The gas to be measured contacts the electrode (wetted by the electrolyte) on the other side of the cathode 14a. The voltage applied between 18a and 18b is approximately 1.5 VDC. Water in the region adjacent to the electrode 18a is reduced resulting in a film of hydrogen ions on the surface. Any dissolved oxygen in the electrolyte which would ordinarily diffuse through and contact the electrode 14a reacts with the hydrogen at the barrier electrode 18a to form water. The oxygen produced at the anode 18b effervesces from the reservoir.

The invention relates to any application to remove interferring components, such as $O_2$ or $H_2$, in an electrolyte which would interfere with the measurement of the desired component from the gas phase. The unwanted component in the electrolyte is prevented from contacting the sensing electrode. It maintains the electrolyte in the condition that enhances the function of a specific electrochemical reduction of $O_2$ from the gas sample.

Having described my invention, what I now claim is:

1. In an electrolytic cell where an electrolytic current is generated between the sensing electrodes, and one of the electrodes is a sensing electrode specific to a component to be measured, and the electrolyte contains that component, thereby interferring with the measuring, the improvement which comprises:
   a first barrier electrode interposed between the sensing electrode specific to the component to be measured and the electrolyte;
   a second electrode disposed in said electrolyte; and means to generate an electrolysis current between the first and second electrode independent of the electrolytic path between the sensing electrodes, the first barrier electrode positioned such that the unwanted components migrating to the sensor electrode are electrolytically inhibited from interferring with the sensing reaction.

2. The cell of claim 1 which comprises:
a reservoir of electrolyte in communication with the electrolyte of the cell and wherein the second electrode is disposed in the electrolyte of the reservoir.

3. The cell of claim 2 wherein the electrode in the reservoir is an anode.

4. The cell of claim 1 where the first barrier electrode is a platinum screen.

5. The cell of claim 3 where the second electrode is a platinum wire.

6. The cell of claim 1 where the electrolyte in the cell is caustic.

7. The cell of claim 1 wherein the sensor electrode specific to the component to be measured is catalytically specific to oxygen analysis.

8. The cell of claim 7 wherein the means to create the current between the first and second electrodes comprises:
means to apply a voltage of about 1.5 volts D.C. between said electrodes; and
means to introduce the fluid carrying the oxygen to be analyzed onto one side of the catalytically specific sensor electrode, and the barrier electrode is disposed on the other side of said sensor electrode between the sensor electrode and the electrolyte.

9. The cell of claim 7 where the catalytically specific sensor electrode is semi-permeable.

10. The cell of claim 7 where the catalytically specific sensor electrode is a cathode.

11. The cell of claim 7 where the non-specific sensor electrode is selected from the materials in the group consisting of Carbon-TFE, platinum or gold.

12. A method for the electrolytic measurement of a component in a fluid stream which includes:
(a) providing an electrolytic cell having a pair of sensor electrodes, one electrode specific for a component to be analyzed in a fluid stream, the sensor electrodes completing a first electrolytic path;
(b) providing a first barrier electrode and a second electrode, the barrier electrode interposed between the sensing electrode specific for the component to be analyzed and the electrolyte, the first and second electrodes defining a second electrolytic path, the function of which is independent of the function of the first electrolytic path; and
(c) applying a voltage across the first and second electrodes to activate the barrier electrode such that unwanted components in the electrolyte are electrolytically inhibited from flowing to the sensing cathode.

13. The method of claim 12 which includes:
providing a reservoir of electrolyte in communication with the electrolyte of the cell and wherein the second electrode is disposed in the reservoir, the electrolytes of the cell and the reservoir being in fluid flow communication.

14. The method of claim 12 which includes;
flowing a gaseous stream comprising oxygen in contacting engagement with one side of the sensing electrode;
measuring the amount of oxygen in the stream electrochemically; p1 ionizing the region on the other side of said sensing electrode and adjacent to the first barrier electrode to form a film of hydrogen on said first barrier electrode while generating oxygen at the second electrode, the hydrogen reacting with the dissolved oxygen in the electrolyte to form water.

15. The method of claim 14 where the oxygen generated at the second electrode effervesces from the reservoir.

16. The method of claim 14 where the current between the barrier electrode and the second electrode is equivalent to the equilibrium rate of $O_2$ available at the barrier electrode.

17. The method of claim 14 where the gas flow rate is between 1.0 and 3.0 scfh.

18. The method of claim 14 where the gas is at a temperature between 0° and 150° F.

19. The method of claim 14 where the gas is at a pressure of less than 15.7 psia.

20. The method of claim 12 where the voltage across the second electrolytic path is less than 1.7 VDC.

* * * * *